US009588116B2

(12) United States Patent
Martins-Filho et al.

(10) Patent No.: US 9,588,116 B2
(45) Date of Patent: Mar. 7, 2017

(54) DIFFERENTIAL DIAGNOSTIC METHOD AND KIT FOR INFECTIOUS AND PARASITIC DISEASES, USING FLOW CYTOMETRY

(71) Applicant: Fundacao Oswaldo Cruz, Rio de Janeiro, RJ (BR)

(72) Inventors: Olindo Assis Martins-Filho, Minas Gerais (BR); Andrea Teixeira de Carvalho, Minas Gerais (BR); Roberta Dias Rodrigues Rocha, Minas Gerais (BR); Marileia Chaves Andrade, Minas Gerais (BR); Danielle Marquete Vitelli Avelar, Belo Horizonte (BR); Stefan Michael Geiger, Minas Gerais (BR); Fernanda Freire Campos Nunes, Belo Horizonte (BR); Marcio Sobreira Silva Araujo, Belo Horizonte (BR); Anna Barbara de Freitas Carneiro Proietti, Minas Gerais (BR); Claudia Di Lorenzo Oliveira, Minas Gerais (BR); Ester Cerdeira Sabino, Sao Paulo (BR); Elenice Moreira Lemos, Espirito Santo (BR)

(73) Assignee: Fundacao Oswaldo Cruz, Rio de Janeiro (BR)

( * ) Notice: Subject to any disclaimer, the term of this patent is extended or adjusted under 35 U.S.C. 154(b) by 0 days.

(21) Appl. No.: 14/385,420

(22) PCT Filed: Mar. 12, 2013

(86) PCT No.: PCT/BR2013/000074
§ 371 (c)(1),
(2) Date: Sep. 15, 2014

(87) PCT Pub. No.: WO2013/134839
PCT Pub. Date: Sep. 19, 2013

(65) Prior Publication Data
US 2015/0057174 A1 Feb. 26, 2015

(30) Foreign Application Priority Data

Mar. 13, 2012 (BR) .............................. 102012005567

(51) Int. Cl.
*G01N 33/569* (2006.01)
*G01N 21/64* (2006.01)

(52) U.S. Cl.
CPC ....... *G01N 33/56905* (2013.01); *G01N 21/64* (2013.01); *G01N 21/6428* (2013.01); *G01N 33/569* (2013.01); *G01N 2469/20* (2013.01)

(58) Field of Classification Search
CPC ........... G01N 33/56905; G01N 33/569; G01N 21/6428; G01N 21/64; G01N 2469/20
See application file for complete search history.

(56) References Cited

FOREIGN PATENT DOCUMENTS

WO 9613615 A1 5/1996

OTHER PUBLICATIONS

Pissinate et al. Upgrading the flow-cytometric analysis of anti-Leishmania immunoglobulins for the diagnosis of American tegumentary leishmaniasis. Journal of Immunological Methods 336 (2): 193-202 (2008).*
Lemos et al., "Detection of Anti-Leishmania (Leishmania) chagasi Immunoglobulin G by Flow Cytometry for Cure Assessment following Chemotherapeutic Treatment of American Visceral Leishmaniasis", Clinical and Vaccine Immunology, vol. 14, No. 5, pp. 569-576 (2007).
Martins-Filho, et al., "Flow Cytometry, a New Approach to Detect Anti-Live Trypomastigote Antibodies and Monitor the Efficacy of Specific Treatment in Human Chagas' Disease", Clinical and Diagnostic Laboratory Immunology, vol. 2, No. 5, pp. 569-573 (1995).
Pissinate et al., "Upgrading the flow-cytometric analysis of anti-Leishmania immunoglobulins for the diagnosis of American tegumentary leishmaniasis", Journal of Immunological Methods, vol. 336, pp. 193-202 (2008).
Rocha et al., "Anti-live Leishmania (Viannia) braziliensis promastigote antibodies, detected by flow cytometry, to identify active infection in American cutaneous leishmaniasis", Revista da Sociedade Brasileira de Medicina Tropical, vol. 35, No. 6, pp. 551-562 (2002).
Vitelli-Avelar et al., "Non-conventional flow cytometry approaches to detect anti-Trypanosoma cruzi immunoglobulin G in the clincal laboratory", Journal of Immunological Methods, vol. 318, pp. 102-112 (2007).
International Search Report for PCT/BR2013/000074 dated Jul. 12, 2013.

* cited by examiner

*Primary Examiner* — Gail R Gabel
(74) *Attorney, Agent, or Firm* — Caesar Rivise, PC

(57) ABSTRACT

The present invention relates to a differential diagnostic method using flow cytometry, performed by means of differential fluorescent marking of biological agents, such as cells and pathogens of interest, with fluorescent substances. The diagnostic method generally consists in performing fluorescent marking of biological agents with gradual concentrations of fluorescent substances, and in analyzing the reactivity profile of IgG1 to the biological agents. The present invention further relates to a diagnostic kit.

5 Claims, 9 Drawing Sheets

(A) Indirect immunofluorescence reaction by flow cytometry (B) Data analysis

FC-Triplex-IgG1 - *Performance of Lot 1*

Reactivity of IgG1 anti -*L.chagasi*
Dilution of serum 1:32.000

Reactivity of IgG1 anti -*T.cruzi*
Dilution of serum 1:2.000

Reactivity of IgG1 anti -*L.amazonensis*
Dilution of serum 1:1.000

FC-Triplex-IgG1 - *Performance of Lot 2*

FC-Triplex-IgG1 - *Performance of Lot 1*

Reactivity of IgG1 anti -*L.chagasi*
Dilution of serum 1:32.000

Reactivity of IgG1 anti -*T.cruzi*
Dilution of serum 1:2.000

Reactivity of IgG1 anti -*L.braziliensis*
Dilution of serum 1:1.000

Reactivity of IgG1 anti -L.chagasi
Dilution of serum 1:32.000

Reactivity of IgG1 anti -T.cruzi
Dilution of serum 1:2.000

Reactivity of IgG1 anti -L.braziliensis
Dilution of serum 1:1.000

Fluorimetric Stability of Trypanosomatids preparation

A

FITC SYSTEM – Storage of isolated parasites stored at –20°C

B

FITC SYSTEM – Storage of Parasite mixture

Fluorimetric Stability of Trypanosomatids preparations

A

B

DIFFERENTIAL DIAGNOSTIC METHOD AND KIT FOR INFECTIOUS AND PARASITIC DISEASES, USING FLOW CYTOMETRY

FIELD OF INVENTION

This invention refers to a method for diagnosis of infectious and parasitic diseases using flow cytometry for simultaneous diagnosis of pathologies using differential fluorescent labeling of biological agents, such as cells and pathogens of interest, with fluorescent substances. In general, the diagnosis method consists in performing the fluorescent labeling of biological agents with incremental concentrations of fluorescent substances, and analyzing the reactivity profile of IgG1 present in the serum of patients with the concerned biological agents.

This invention also provides a diagnosis kit that has preparations of biological agents stained with incremental concentrations of fluorescent substance; a preparation of human biotinylated antibody anti-IgG1; fluorescent reagent for the detection of human anti-IgG1; serum samples from negative control subjects; serum samples from a positive control subject; a solution to wash the plates and dilute the samples; a fixative solution for the preparation for flow cytometry reading; 96-well plates and sealing adhesives.

BACKGROUND OF THE INVENTION

Laboratory reactivity of serum samples from patients with certain diseases can often be very similar. This is mainly due to the antigenic sharing among agents related to the etiology of such diseases. In these cases, conventional serological methods of diagnosis have as main disadvantage the low specificity, contributing to false-positive results and difficulties in differential and confirmatory serologic diagnosis of the disease.

For example, the laboratory diagnosis of Chagas' disease, especially in the chronic phase of infection, based on the use of serological methods for detection of anti-*T. cruzi*. According to the Brazilian Consensus on Chagas Disease (Brazilian Consensus in Chagas Disease—Surveillance Department of the Ministry of Health, Journal of the Brazilian Society of Tropical Medicine VOL. 38: SUPPLEMENT III, 2005), serologic tests of choice for diagnosing the disease are: Indirect Hemagglutination (IHA), the Indirect Immunofluorescence Assay (IFA) and Enzyme-Linked Immunosorbent Assay (ELISA). These tests, known as conventional, are commonly used in the diagnosis of Chagas' disease in clinical laboratories and serological screening in blood banks. When applied together, they show high sensitivity, however, due to the large antigenic sharing among parasites belonging to the Tripanosomatidae family, as is the case of *Leishmania* spp.; conventional serological methods of diagnosis have as main disadvantage the low specificity, contributing to false-positive results and difficulties in differential and confirmatory serologic diagnosis of the Chagas' disease and leishmaniasis (Marchi et al, 2007). This issue gains even greater proportions when designed in the reality of co-endemic regions for Chagas' disease and leishmaniasis, which is reaching global dimensions as a result of the processes of population migration and environmental changes.

The application of two tests of distinct principles for the diagnosis of *T. cruzi* infection in Blood Banks, as recommended by the Brazilian Ministry of Health, allowed the desired decrease in transmission of Chagas' disease by blood transfusion; on the other hand, a new problem arose, associated with the increase in the number of patients with inconclusive or non-negative serological results. Thus, a major problem in serological screening for Chagas' disease in blood donors is the high frequency of non-negative or indeterminate reactions, which causes many healthy subjects to be stained as suffering from a serious illness, and promotes significant unnecessary discarding of blood units in blood banks and major financial losses for the health system.

Searching the scientific literature, one can notice the difficulty of eliminating cross-reactivity in immunofluorescence analysis by flow cytometry of trypanosomatids when this technique is applied to the diagnosis of *T. cruzi* infection or for the diagnosis of some species of *Leishmania* sp., and there is no description of diagnostic of the three diseases simultaneously by the method of immunofluorescence by flow cytometry.

Thus, there is a clear need for a technical solution that allows the use of flow cytometry, a technique with high sensitivity and specificity for the simultaneous diagnosis of pathologies in which the specific antibodies to be detected are directed at targets, or biological agents, morphologically similar.

The literature points to "Luminex" technology (Bonetta, L., Flow Cytometry smaller and better. Nature Methods 2(10): 785-795, 2005), that also uses a system of incremental labeling with fluorochromes as a facilitator to conduct multiple analyzes on a single platform of reaction for immunofluorescence by flow cytometry. However, the LUMINEX system differs from the triplex method for using microspheres incrementally stained with fluorochromes bound to antibodies or antigens, not aiming at the incremental labeling directly in the target biological agent of antibody reactivity, such as the Triplex method does. Furthermore, there are no assays using the Luminex method, using fluorescent microspheres bound to antigenic constituents derived from pathogens, specifically excreted or secreted antigens (ES-antigens), as well as selective antigens of plasma membrane of pathogens free of contamination with antigens derived from other cellular compartments, which can be achieved with the Triplex method. In addition, in the invention described herein the labeling can be carried out directly using the full parasite, such that the antigenic diversity available to assist in the detection is increased.

The triplex method also has the potential of incorporating the "multiplex" mode with the insertion of new molecular targets, then allowing the simultaneous detection of IgG1 reactivity against other pathogens, such as Tachyzoites of *Toxoplasma gondii*, spirochete of *Treponema pallidum* and even target cells infected with HTLV. These represent a practical application of the triplex method in screening assays in blood banks.

The high number of inconclusive reactions reinforces the real and urgent need to develop more specific serological tests or practical and rapid confirmatory tests, which can be introduced in clinical laboratories routine and blood bank services, reducing unnecessary disposal of blood bags and the difficulty in conducting donors with indeterminate reactions.

SUMMARY OF INVENTION

This invention refers to a method for diagnosis of infectious and parasitic diseases using flow cytometry for simultaneous diagnosis of pathologies using differential fluorescent labeling of biological agents, such as cells and pathogens of interest morphologically similar, capable of being broken down by differential labeling with fluorescent substances. In general, the diagnosis method consists in performing the fluorescent labeling of the agents with incremental concentrations of fluorescent substances, and analyzing the reactivity profile of IgG1 present in the serum of patients with the concerned biological agents. The development is performed by anti-IgG1 antibodies conjugated to a fluorochrome that is detected by fluorescence channel of the flow cytometer different from that applied to discriminate the target biological agents of antibodies.

After labeling the biological agents, the samples are analyzed in a flow cytometer. Biological agents are discriminated for being stained with incremental concentrations of fluorescent substance, so they can be differentially identified even though they show similar morphometric patterns. The analysis of the reactivity of antibodies is initially performed by the selection of the population of interest through size, granularity and fluorescence parameters. Subsequently, the detection of antibodies bound to each specific population of interest is made by reading the fluorescence emitted by the IgG1 revelation system in distinct fluorescence channel, which shows the percentage of positive fluorescent targets. The percentage of positive fluorescent targets must not exceed 2% in the negative control, so that the percentage displacement determines the positive sera for each pathology.

The results are evaluated from a desynchronized algorithm that allows conclusions about the serologic reactivity of the samples. In the algorithm adopted, it is performed a concomitant research of IgG1 specific antibodies for different biological agents in the same serum sample.

The method proposed by this invention uses biological agents that once stained with different fluorochrome concentrations are combined in a single platform, allowing simultaneous analysis of different antibodies in sera of patients in a single immunofluorescence test, employing flow cytometry as method of segregating the sample and amplifying the fluorescence signals in the stages of reading.

Fluorescent substances in accordance to this invention include fluorescent dyes or fluorochromes selected from Alexa-fluor, Fluorescein Isothiocyanate, Chicago Sky Blue, Rhodamine, Phycoerythrin, and Allophycocyanine.

The method of this invention can be used to differentiate a number of pathogens, assuming a Multiplex mode, incorporating the diagnosis of other infectious and parasitic diseases, such as toxoplasmosis, syphilis, HIV, HTLV-1 and HTLV-2 in the same kit where the user can select which agents will be tested in a given reaction, according to the sample in question and the type of screening to be made.

This invention also provides a diagnosis kit that have preparations of biological agents (in the case exemplified, the parasites stained with incremental concentrations of fluorescent substance), a preparation of human biotinylated antibody anti-IgG1, fluorescent reagent for the detection of human anti-IgG1, serum samples from negative control subjects, serum samples from positive control subjects, a solution to wash the plates and dilute the samples, a fixative solution for the preparation for flow cytometry reading, 96-well plates and sealing adhesives.

In a preferred embodiment, the invention provides a method for the diagnosis of Leishmaniasis and Chagas' disease. More particularly, this invention refers to a method for serological diagnosis of Chagas' disease, Cutaneous Leishmaniasis, and Visceral Leishmaniasis employing immunofluorescence by flow cytometry.

The method of this invention consists in simultaneous research of antibodies IgG1 anti-*Leishmania chagasi*, anti-*Trypanosoma cruzi*, and anti-*Leishmania amazonensis* or *Leishmania braziliensis*.

The diagnosis method by flow cytometry of this invention is herein referred to as FC-Triplex-IgG1.

With the method of this invention it is possible to simultaneously diagnose three pathologies though the incremental labeling of targets (pathogens) with fluorescent dyes. The method of the invention allows the placement of a label on the region correspondent to the mixed population of trypanosomatids and analysis of the IgG1 reactivity profile, by determination of the PPFP (percentage of positive fluorescent parasites) relative to the fluorescence of the label used in the anti-IgG1 antibody. For interpreting the results, the method FC-Triplex-IgG1 proposes the use of a desynchronized algorithm for analysis of the serological reactivity of samples.

One of the advantages of the present invention is that from the method proposed herein it is possible to exclude subjects with Visceral Leishmaniasis and Cutaneous Leishmaniasis in serological screening for Chagas' disease in blood and tissues banks, given the high frequency of non-negative or indeterminate reactions.

BRIEF DESCRIPTION OF FIGURES

Aspects of the present invention will now be described to serve as example with reference to the accompanying drawings, in which:

FIG. 4A shows the results of performing the serological test algorithm CF-Triplex-IgG1 on a first lot of serum and FIG. 4B shows the results of performing the serological test algorithm CF-Triplex-IgG1 on a second lot of serum.

FIG. 5A shows the results of performing the serological test algorithm CF-Triplex-IgG1 on a first lot of serum and FIG. 5B shows the results of performing the serological test algorithm CF-Triplex-IgG1 on a second lot of serum.

DETAILED DESCRIPTION OF THE INVENTION

Figure 1A:
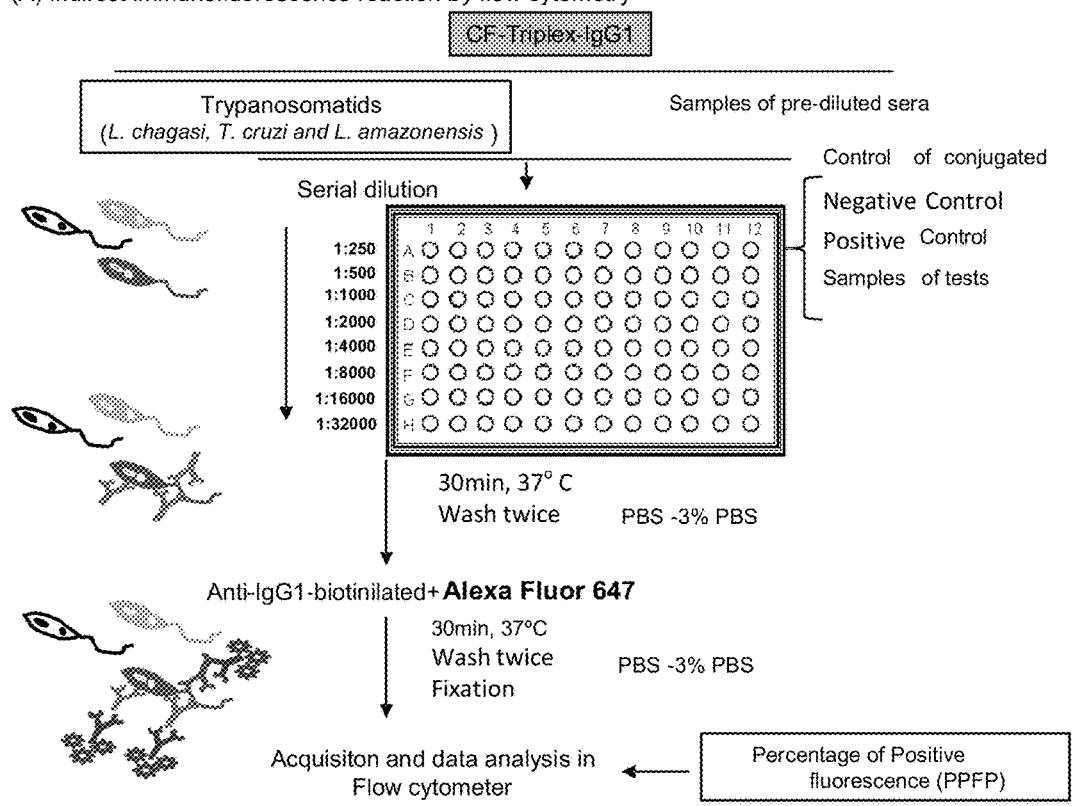
FIG. 1A is a schematic representation of indirect immunofluorescence by flow cytometry, in which the parasites are stained with Fluorescein isothiocyanate (FITC) and biotinylated anti-IgG antibodies are conjugated to Alexa Fluor647.

This invention refers to a diagnosis method for simultaneous research of IgG1 antibodies anti-*Trypanosoma cruzi*, anti-*Leishmania chagasi* and anti-*Leishmania amazonensis* (or *Leishmania braziliensis*) in single platform, by flow cytometry, referred to herein as Triplex Method (FC-Triplex-IgG1).

The method for differential diagnosis in this invention consists of a method of immunofluorescence by flow cytometry employing differential and incremental labeling of biological agents with fluorescent substances comprising the following steps:

(a) differential labeling of biological agents with incremental concentrations of fluorescent substance;

(b) preparation of a mixed suspension of the biological agents stained in the previous step (a);

(c) incubation of the biological agents mixed suspension with serial dilutions of heat-inactivated human serum;

(d) incubation of the suspension obtained in the step (c) with human antibody anti-IgG1 conjugated with biotin, in the presence of streptavidin conjugated with fluorescent substance;

(e) incubation of the biological agents obtained in step (d) with fixative solution for cytometry;

(f) obtaining size parameters, granularity and fluorescence during analysis of samples of biological agents on flow cytometric equipment;

(g) analysis of the IgG1 reactivity profile, by determination of the percentage of positive fluorescent biological agents (PPFP) relative to the fluorescence of the label used in the anti-IgG1; and, (h) analysis of results using a desynchronized algorithm for analysis of the serological reactivity of sera relative to the biological agents.

In a specific embodiment, the invention is a method of indirect immunofluorescence reaction, by flow cytometry, performed in a liquid suspension, which employs in a single platform epimastigotes of *T. cruzi*, promastigotes of *L. chagasi*, promastigotes of *L. amazonensis* and *L. braziliensis*, previously fixed and stained with incremental concentrations of fluorochrome fluorescein isothiocyanate—FITC (FL-1) or fluorochrome Alexa fluor 647 (FL-4), for simultaneous research of IgG1 antibodies anti-*T. cruzi*, anti-*L. chagasi* and *L. amazonensis* or anti-*L. braziliensis*.

The invention will now be described based on examples, which should not be construed as limiting its scope.

Example 1

Preparing the Samples

Study Population.

For the establishment and standardization of method CF-Triplex-IgG1, 80 serum samples belonging to the serum bank CPqRR/FIOCRUZ were used. The serum samples were organized in four groups: the group Pool NI was composed of a mixture of 20 serum samples from healthy subjects, the group Pool CH was composed of a mixture of 20 sera from patients with Chagas' disease, the Pool LTA group was composed of a mixture of 20 sera of patients with American Cutaneous Leishmaniasis and Pool LV group was composed of a mixture of 20 patients with Visceral Leishmaniasis.

Collection and Processing of Samples.

Serum samples were inactivated at 56° C. by 30 min and centrifuged at 14,000 rpm at 4° C. for 5 min to remove particles. After centrifugation, the supernatant was aliquoted and stored at −20° C. until their use in flow cytometry assays. At the moment of utilization, the samples were thawed, diluted in buffered saline solution with phosphate-PBS supplemented with 3% fetal calf serum (FCS—Sigma Co. USA) centrifuged at 4° C., 14,000 rpm for 5 min and the supernatants were used in flow cytometry (Cordeiro et al. 2001).

Cultivation of *Trypanosoma cruzi* Epimastigotes.

Epimastigote forms of *T. cruzi* were obtained from complex liquid culture liver infusion tryptose (LIT) and incubated in a BOD chamber (model 347) at 28° C.±1° C. Every seven days of cultivation, a spike of 1.0×106 parasites/mL was performed, and the culture maintained in successive passages in medium LIT.

Cultivation of promastigote forms of *Leishmania amazonensis* (or *Leishmania brasiliensis*) and *Leishmania chagasi*.

Promastigote forms of *L. amazonensis* (or *L. brasiliensis*) and *L. chagasi* were obtained from blood agar culture, Novy-MacNeal-Nicolle associated to medium LIT (NNN-LIT) and incubated in a BOD chamber (model 347) at ±1° C. Every two days of cultivation, a spike of 5.0×106 parasites/mL was performed for the medium NNN-LIT or for the medium NNN associated to the medium M199 (NNN-M199). The culture was maintained in successive passages through NNN-LIT or NNN-M199.

Preparation of epimastigotes forms of *T. cruzi* and the promastigote forms of *L. amazonensis* (or *L. brasiliensis*) and *L. chagasi* for immunofluorescence assay by flow cytometry.

Epimastigotes forms of *T. cruzi* with seven days of cultivation in medium LIT (Vitelli, 2007) and promastigotes forms of *L. amazonensis* (or *L. brasiliensis*) and *L. chagasi* with two days of culture in medium NNN-M199 were transferred separately for three 50 mL polypropylene tubes (Falcon®) and homogenized in a vortex at low speed (speed 3) to break up the lumps. Then, the suspensions were subjected to differential centrifugation (25° C., 200 rpm for 10 minutes) to remove erythrocytes and dead parasites in the sediment. For recovery of the parasites in the supernatant, they were left to stand for 30 minutes at room temperature. The supernatants were transferred to other 50 mL polypropylene tube and the pellet was discarded. Then, the parasites were washed in PBS twice, centrifugation at 4° C., 2500 rpm for 10 minutes. The supernatants were discarded and the pellets formed were carefully homogenized and resuspended in PBS. Suspensions of epimastigotes forms of *T. cruzi* and promastigotes forms of L. amazonensis (or L. brasiliensis) and L. chagasi were adjusted to 1.0×107 parasites/ml in PBS and fixed in a fixative solution Macs Facs Fix (MFF).

Differential staining of epimastigotes forms of T. cruzi and the promastigote forms of L. amazonensis (or L. brasiliensis) with fluorescein isothiocyanate (FITC).

Suspensions of 1.0×107 parasites/mL of epimastigotes of T. cruzi and of 1.0×107 parasites/mL of promastigote of L. amazonensis (or L. brasiliensis) in PBS were incubated with different concentrations of fluorescein isothiocyanate-FITC (100 µg/mL to 0.1 µg/mL) for 30 minutes, at 37° C., protected from light. After incubation, the parasites were washed PBS by centrifugation (4° C., 2500 rpm, 10 minutes) and incubated with PBS 10% FCS for 30 minutes, at room temperature, for fixation of the fluorochrome to the proteins of the trypanosomatids. After incubation, the parasites were washed PBS by centrifugation (4° C. 2500 rpm, 10 minutes). The supernatants were discarded and the pellets formed were carefully homogenized and resuspended in PBS. At the end of the washing steps, epimastigotes forms and promastigotes forms were adjusted to a suspension of $5.0 \times 10^6$ parasites/mL in PBS 3% FCS for assays of the flow cytometer.

Example 2

Figure 2A:
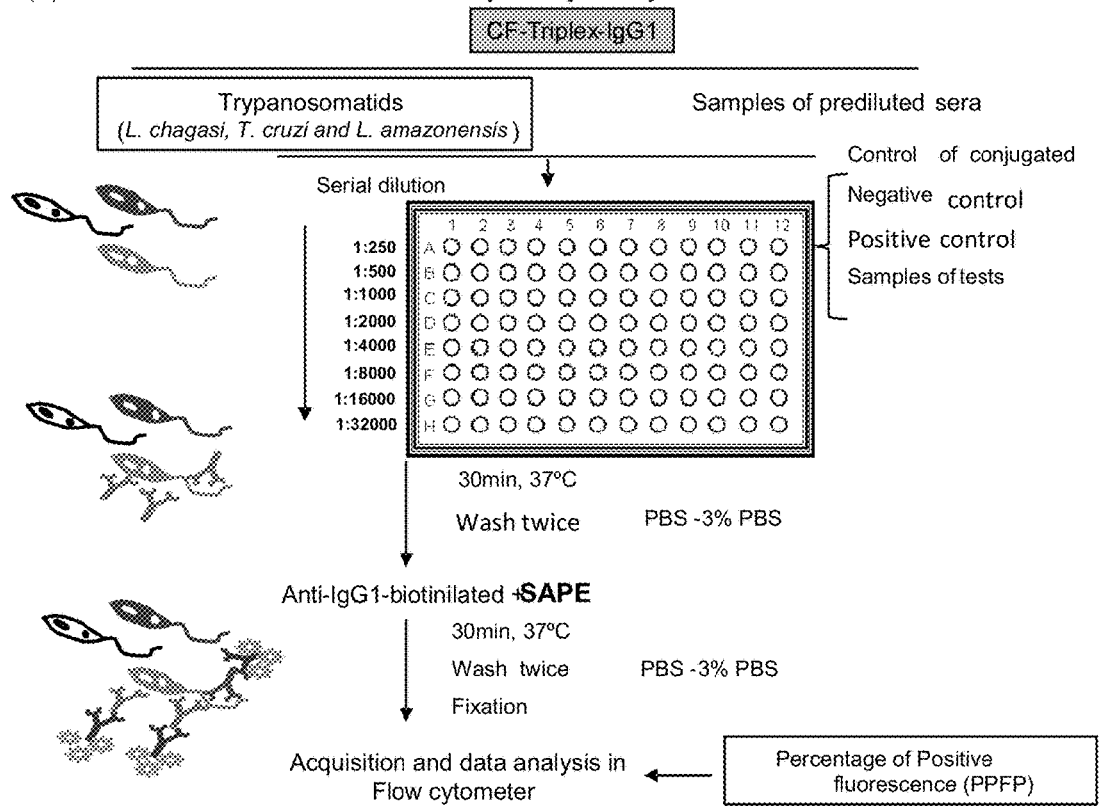
FIG. 2A is a schematic representation of indirect immunofluorescence by flow cytometry, in which the parasites are stained with Fluorescein isothiocyanate (FITC) and biotinylated anti-IgG antibodies are conjugated to SAPE.

Study of IgG1 Antibodies Anti-Fluorescent Trypanosomatids Mixed Suspension by Flow Cytometry To perform the indirect immunofluorescence reaction, by flow cytometry, a mixed suspension, prepared as in Example 1, with 50 µL trypanosomatids consisted of promastigotes forms of L. chagasi, epimastigotes forms of T. cruzi and promastigotes forms of L. amazonensis (or L. braziliensis) are incubated with 50 µL heat-inactivated human serum, in dilutions 1:250 to 1:32000 in PBS 3% FCS for 30 minutes, at 37° C., protected from light. After incubation with the serum, the parasites were washed twice with 150 µL PBS 3% FCS by centrifugation at 18° C., 2200 rpm, 10 min, and the supernatant was discarded. For development of IgG1 binding to the surface of parasites, the incubation is performed for 30 minutes, at 37° C., protected from light, in the presence of 50 µL of monoclonal human antibody anti-IgG1 conjugated with biotin, diluted at 1:6400 in PBS-3% FCS in the presence of 20 µL of streptavidin conjugated to Alexa fluor 647, diluted at 1:1000 in PBS 3% FCS or streptavidin conjugated to phycoerythrin (SAPE), diluted at 1:400 PBS 3% FCS—FIG. 1A and FIG. 2A, respectively. After incubation, the parasites are washed twice again with 150 µL PBS 3% FCS by centrifugation at 18° C., 2200 rpm, 10 min, and the supernatant was discarded. The parasites are then resuspended with 200 µL of fixative solution for cytometry—MFF and the samples are kept at 4° C., protected from light, until the time of reading in the flow cytometer (FACScalibur-Becton Dickinson). The maximum time for data acquisition is a maximum of 24 hours—FIG. 1A and FIG. 2A.

For data analysis, the first challenge was to establish a system of selective analysis of epimastigote forms of T. cruzi and promastigotes forms of Leishmania spp. The morphometric similarity of the trypanosomatids prevented its proper selection using flow cytometry, only parameters of size and granularity. Faced with this challenge, the proposed solution consisted in using a incremental staining system from each parasite population with fluorescence' (FL-1) using fluorescein isothiocyanate—FITC or fluorescence 4 (FL-4) using Alexa Fluor 647, which allowed discrimination of each population of trypanosomatids, which was distinct from the fluorescence system employed for development of serological reactivity of IgG1 after incubation of the parasites with human serum. As described above, the evaluation of the serological reactivity of IgG1 anti-trypanosomatids, development systems with streptavidin conjugated with Alexa Fluor 647 (FL-4) or SAPE (FL-2) were used, respectively—FIG. 1A and FIG. 2A.

Figure 1B:
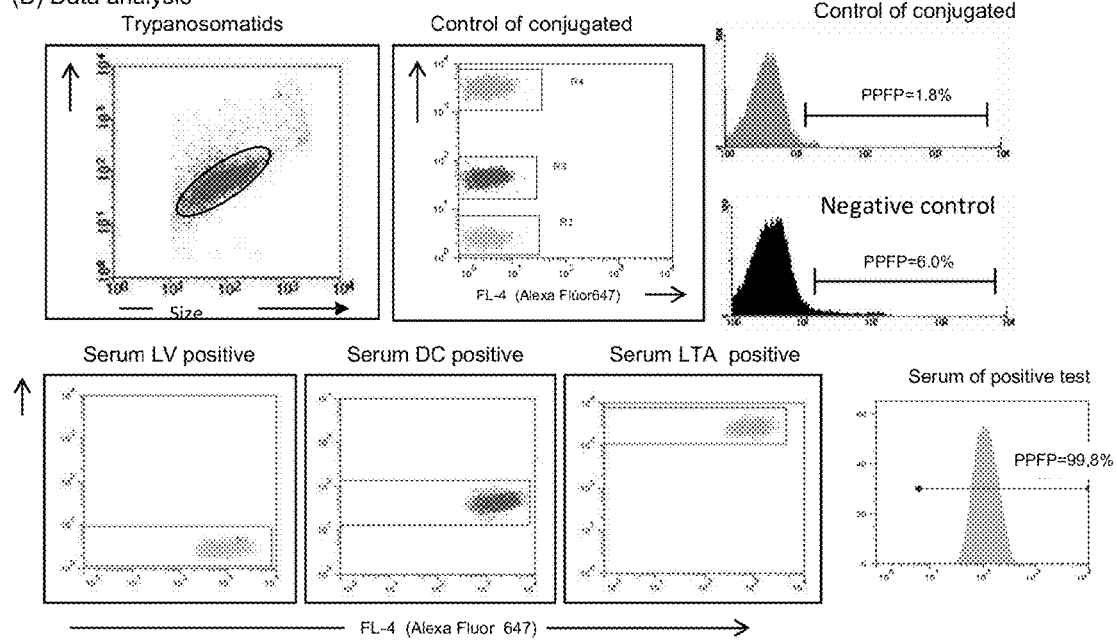
FIG. 1B is a schematic representation of the sequence of analysis of the data obtained by flow cytometry of the reaction shown in FIG. 1A.
Figure 2B:
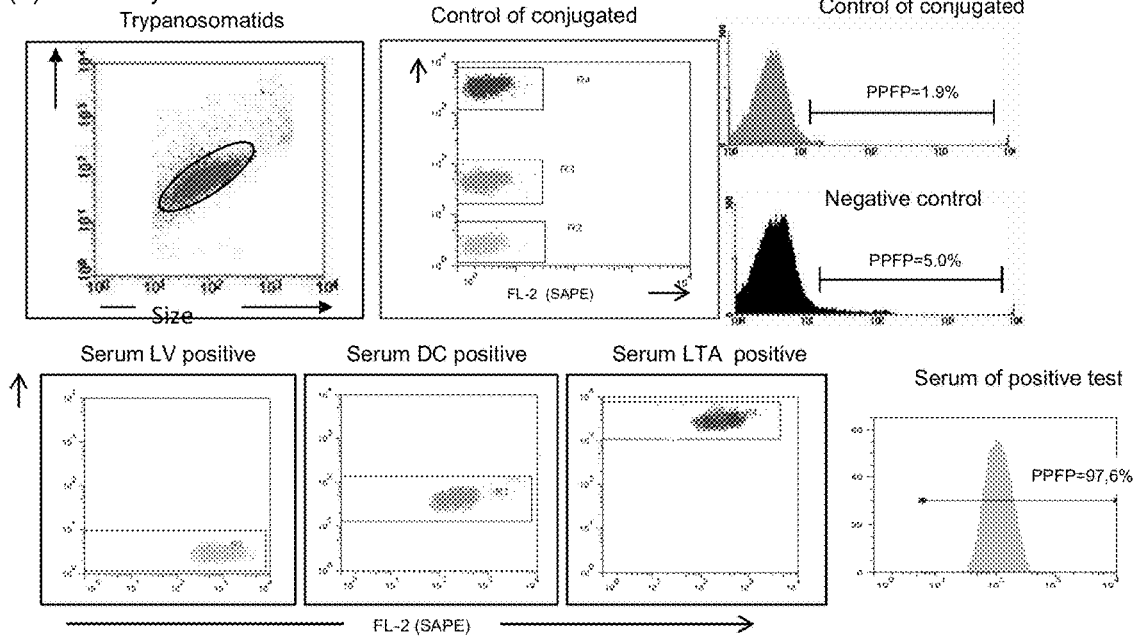
FIG. 2B is a schematic representation of the sequence of analysis of the data obtained by flow cytometry of the reaction shown in FIG. 2A.

Trypanosomatids stained with incremental concentrations of fluorochromes, when combined in a single platform present in size graphics versus granularity, a characteristic and homogeneous distribution, which allows the placement of a stain on the region corresponding to the mixed population of trypanosomatids of interest (R1)—FIG. 1B and FIG. 2B.

For evaluation of parasites stained with FITC (FL-1) using dot plot graphs of FL1 versus FL-4, the parasites that do not emit FL-1 corresponds to promastigote forms of L. chagasi, which allows the placement of a stain on the region corresponding to this population (R2). The parasites that present low fluorescence intensity correspond to the epimastigotes forms of T. cruzi, which allows the placement of a stain on the region corresponding to this population (R3). At last, the parasites that present high fluorescence intensity correspond to the promastigotes forms of L. amazonensis, which allows the placement of a stain on the region corresponding to this population (R4)—FIG. 1B.

The results of the analysis of FL-4 presented by trypanosomatids after incubation with sera were expressed as the percentage of positive fluorescent parasites (PPFP) observed for each individual test with each species of trypanosomatids—L. chagasi, T. cruzi and L. amazonensis (or L. brasiliensis)—in relation to the conjugate control. PPFP was determined for each sample by establishing a negative threshold as a function of the fluorescence curve obtained for the control of the non-specific binding of the conjugate (M1) for each parasite population selected. For each experiment a threshold of reactivity was established of at most 2% of PPFP for the internal control of the reaction (conjugate control)—FIG. 1B.

Then, employing the same label, PPFP values were obtained for the serum sample evaluated. For each set of assays, a new label was positioned using the conjugate control from that experiment. This kind of parameter offers some advantages, such as ease and speed in obtaining results and their reproducibility regarding data obtained from inter-laboratory analyzes or analyzes performed repeatedly—FIG. 1B.

For evaluation of parasites stained with Alexa Fluor 647 (FL-4), using dot plot graphs of FL-4 versus FL-2, the parasites that do not emit FL-4 correspond to promastigote forms of L. chagasi, which allows the placement of a label on the region corresponding to this population (R2). The parasites that present low fluorescence 4 intensity correspond to the epimastigotes forms of T. cruzi, which allows the placement of a label on the region corresponding to this population (R3). At last, the parasites that present high fluorescence 4 intensity correspond to the promastigotes forms of L. amazonensis (or L. braziliensis), which allows the placement of a label on the region corresponding to this population (R4)—FIG. 2B.

The results of the analysis of FL-2 presented by trypanosomatids after incubation with sera were expressed as the percentage of positive fluorescent parasites (PPFP) observed for each individual test with each species of trypanosomatids—L. chagasi, T. cruzi and L. amazonensis (or L. brasil-

*iensis*)—in relation to the conjugate control. PPFP was determined for each sample by establishing a negative threshold as a function of the fluorescence curve obtained for the control of the non-specific binding of the conjugate (M1) for each parasite population selected. For each experiment a threshold of reactivity was established of at most 2% of PPFP for the internal control of the reaction (conjugate control)—FIG. 2B.

Then, employing the same label, PPFP values were obtained for the serum sample evaluated. For each set of assays, a new label was positioned using the conjugate control from that experiment. This kind of parameter offers some advantages, such as ease and speed in obtaining results and their reproducibility regarding data obtained from inter-laboratory analyzes or analyzes performed repeatedly—FIG. 2B.

For interpreting the results, the method FC-Triplex-IgG1 proposes the use of a desynchronized algorithm for analysis of the serological reactivity of samples tested aiming to eliminate cross reactivity in the differential diagnosis of de Chagas' disease, cutaneous leishmaniasis and visceral leishmaniasis. In the algorithm adopted, it is performed a concomitant research for IgG1 anti-*L. chagasi*, anti-*T. cruzi* and anti-*L. amazonensis* or *L. braziliensis* in the same serum sample. The interpretation follows some criteria, described below:

The first evaluation consists of analysis of IgG1 anti-*L. chagasi* reactivity in the dilution of serum 1:32000. Considering the cutoff point of PPFP=60%, given a value of PPFP≥60%, the result is considered positive for visceral leishmaniasis. Given a value of PPFP<60%, the result is considered negative and we can move on to the next step.

Figure 3:
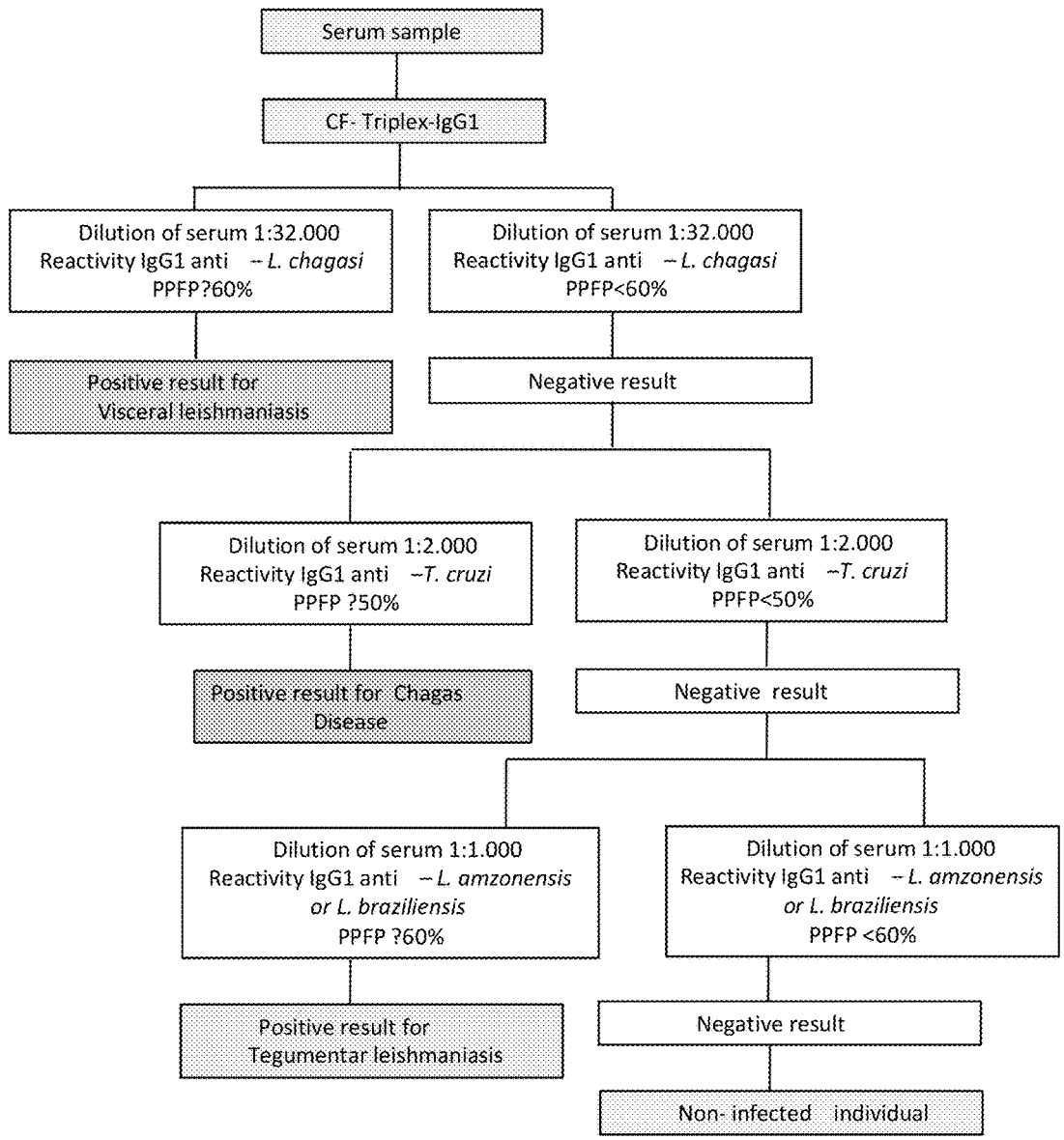
FIG. 3 shows the serological test algorithm CF-Triplex-IgG1 for the detection of IgG1 antibodies anti-*L. chagasi*, anti-*T. cruzi* and anti-*L. amazonensis* or *L. braziliensis*, simultaneously.

The second evaluation consists of analysis of IgG1 anti-*T. cruzi* reactivity in the dilution of serum 1:2000. Considering the cutoff point of PPFP=50%, given a value of PPFP≥50%, the result is considered positive for Chagas' disease. Given a value of PPFP<50%, the result is considered negative and we can move on to the next step. The third evaluation consists of analysis of IgG1 anti-*L. amazonensis* (or *L. braziliensis*) reactivity in the dilution of serum 1:1000. Considering the cutoff point of PPFP=60%, given a value of PPFP≥60%, the result is considered positive for cutaneous leishmaniasis. Given a value of PPFP<60%, the result is considered negative, the serum is classified as non-reactive for the trypanosomatids and therefore the subject is not infected (FIG. 3).

Table 1 presents the possible results of the fluorescence analyzes, expressed in PPFP, presented by the trypanosomatids (*L. chagasi, T. cruzi* and *L. amazonensis* (or *L. braziliensis*)) considering the cutoff points of PPFP=60%, PPFP=50% and PPFP=60%, respectively, after incubation with serum from a patient with visceral leishmaniasis, a patient with Chagas' disease, a patient with cutaneous leishmaniasis and a non-infected subject.

TABLE 1

Possible results of IgG1 anti-trypanosomatides reactivity in sera from patients with VL (visceral leishmaniasis), CD (Chagas' disease), ACL (American cutaneous leishmaniasis) and NI (non-infected).

| Serum | *L. chagasi* (1:32000) ≥60% PPFP | *T. cruzi* (1:2000) ≥50% PPFP | *L. amazonensis* or *L. braziliensis* (1:1000) ≥60% PPFP |
|---|---|---|---|
| VL | + | +/− | +/− |
| CD | − | + | +/− |

TABLE 1-continued

Possible results of IgG1 anti-trypanosomatides reactivity in sera from patients with VL (visceral leishmaniasis), CD (Chagas' disease), ACL (American cutaneous leishmaniasis) and NI (non-infected).

Figure 4A:
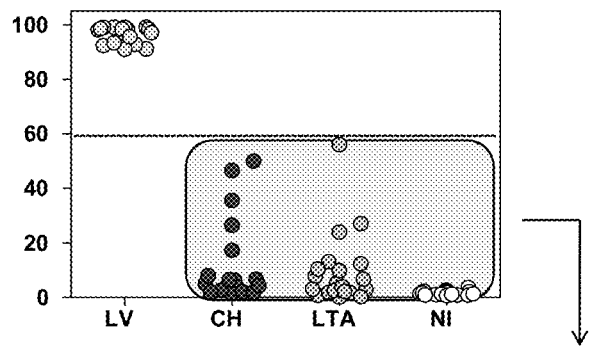
FIG. 4A and FIG. 4B show the reactivity of IgG1 anti-trypanosomatids stained with FITC and revealed with anti-IgG antibodies conjugated to SAPE in individual sera from patients with Visceral Leishmaniasis (VL), Chagas' disease (CH), American Cutaneous Leishmaniasis (ACL) and uninfected subjects.
Figure 4A:
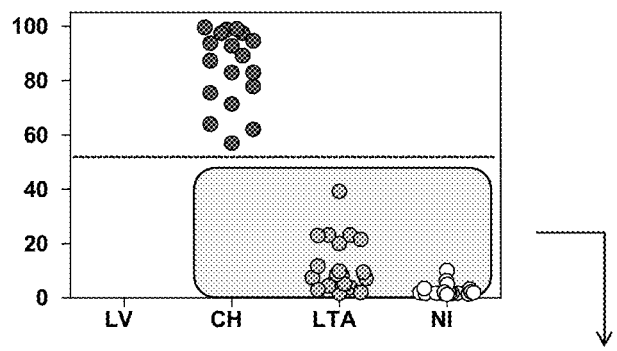
Figure 4A:
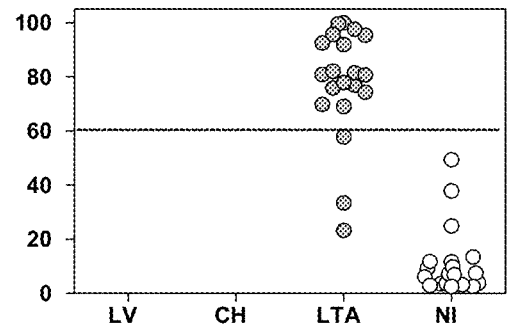
Figure 4B:
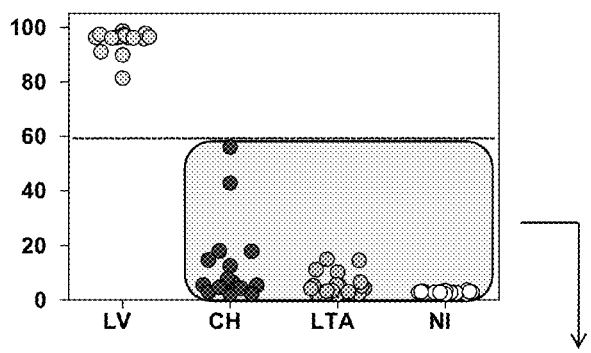
Figure 4B:
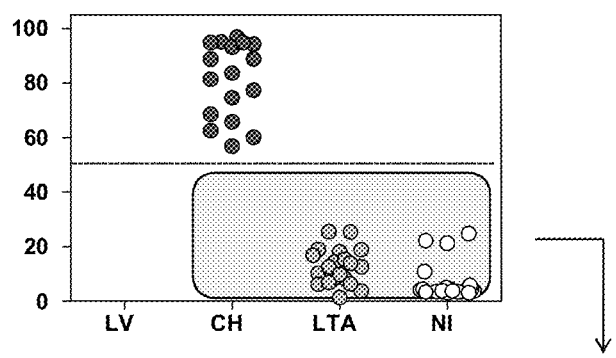
Figure 4B:
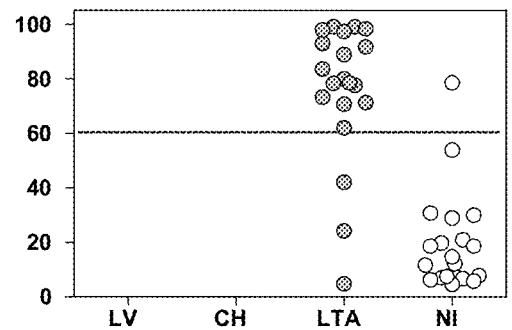

| Serum | *L. chagasi* (1:32000) ≥60% PPFP | *T. cruzi* (1:2000) ≥50% PPFP | *L. amazonensis* or *L. braziliensis* (1:1000) ≥60% PPFP |
|---|---|---|---|
| ACL | − | − | − |
| NI | − | − | − | where:
(+) means the positive result of IgG1 reactivity
(−) means the negative result of IgG1 reactivity
(+/−) means the positive or negative result of IgG1 reactivity The results, repeated and confirmed, with the application of a Triplex system performed with trypanosomatids stained with incremental concentrations of FITC (FL-1) and a revelation system of IgG1 anti-trypanosomatids reactivity with Alexa Fluor 647 (FL-4), showed an excellent performance for the differential serological diagnosis of Chagas' disease, visceral leishmaniasis and cutaneous leishmaniasis. Using 77 serum samples, including negative controls and patients with Chagas' disease, visceral leishmaniasis and cutaneous leishmaniasis, it was possible to identify the high performance of the method, with 96.1% (74/77) and 94.7% (73/76) correct results. In the first batch of parasites, from a total of 77 samples tested, three false-negative results were observed for cutaneous leishmaniasis—FIG. 4A. In the second batch of parasites, from a total of 76 samples tested, three false-negative results were observed for cutaneous leishmaniasis and a false-negative result of a non-infected subject—FIG. 4B.

Figure 5A:
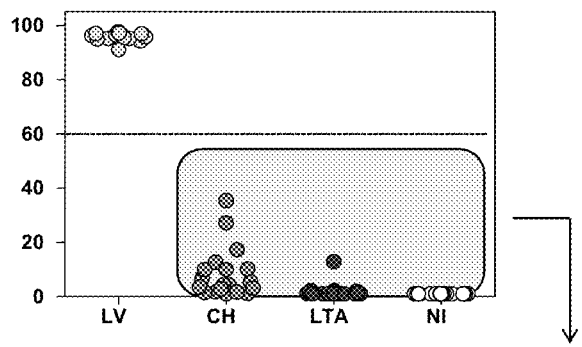
FIG. 5A and FIG. 5B show the reactivity of IgG1 anti-trypanosomatids stained with Alexa Fluor647 and revealed with anti-IgG antibodies conjugated to SAPE in individual sera from patients with Visceral Leishmaniasis (VL), Chagas' disease (CH), American Cutaneous Leishmaniasis (ACL) and uninfected subjects.
Figure 5A:
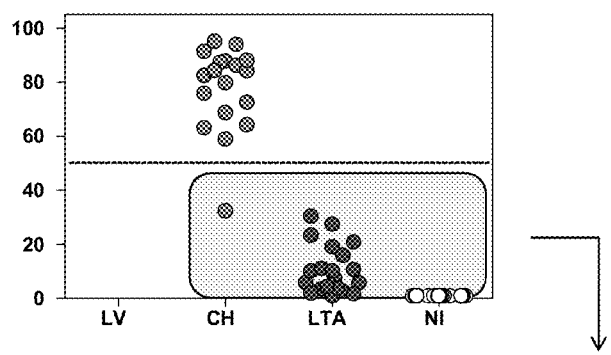
Figure 5A:
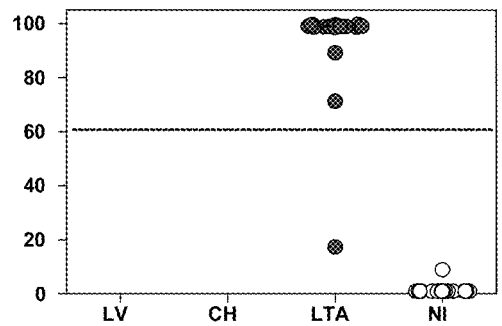
Figure 5B:
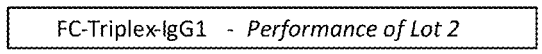
Figure 5B:
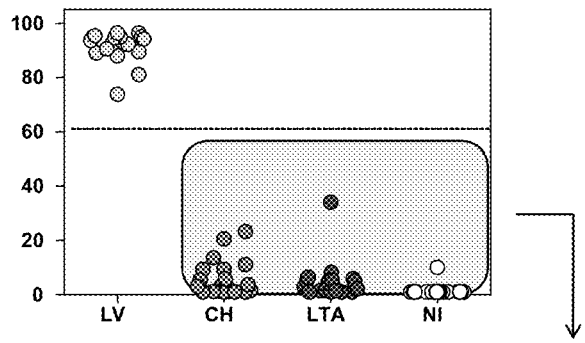
Figure 5B:
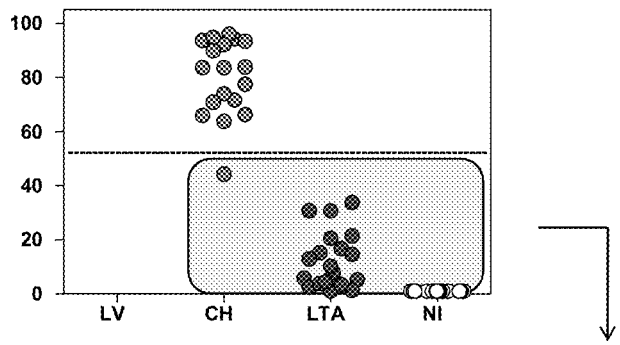
Figure 5B:
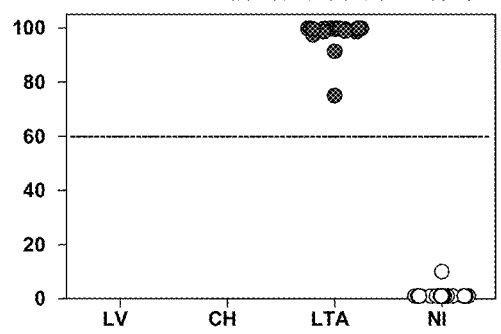

The results, repeated and confirmed, with the application of a Triplex system performed with trypanosomatids stained with incremental concentrations of Alexa Fluor 647 (FL-4) and a revelation system of IgG1 anti-trypanosomatids reactivity with SAPE (FL-2), also showed an excellent performance for the differential serological diagnosis of Chagas' disease, visceral leishmaniasis and cutaneous leishmaniasis. Using 77 serum samples, including negative controls and patients with Chagas' disease, visceral leishmaniasis and cutaneous leishmaniasis, it was possible to identify the high performance of the method, with 98.7% (75/76) correct results, in the first and second batches of parasites—FIG. 5A and Figure BD. From a total of 77 samples tested, it was observed one false-negative result for Chagas' disease—FIG. 5A and FIG. 5B.

Example 3

Stability of Reagents

The purpose of Example 3 was to confirm the stability of staining the parasites with Alexa Fluor-647 and FITC during a period of 12 months and in three storage conditions (room temperature, 4° C., −20° C.). For the performance of these tests, the parasites previously stained with fluorochromes Alexa Fluor-647 and FITC were stored at the three temperatures described above for a period of 12 months. Every month after the beginning of storage, the parasites were taken to the flow cytometer for fluorescence verification. In addition, every three months serology was performed with parasites stored at each temperature. The results show that the fluorimetric profile of FITC staining was stable at the 3 storage conditions tested (room temperature, 4° C. and −20°

Figure 6A:
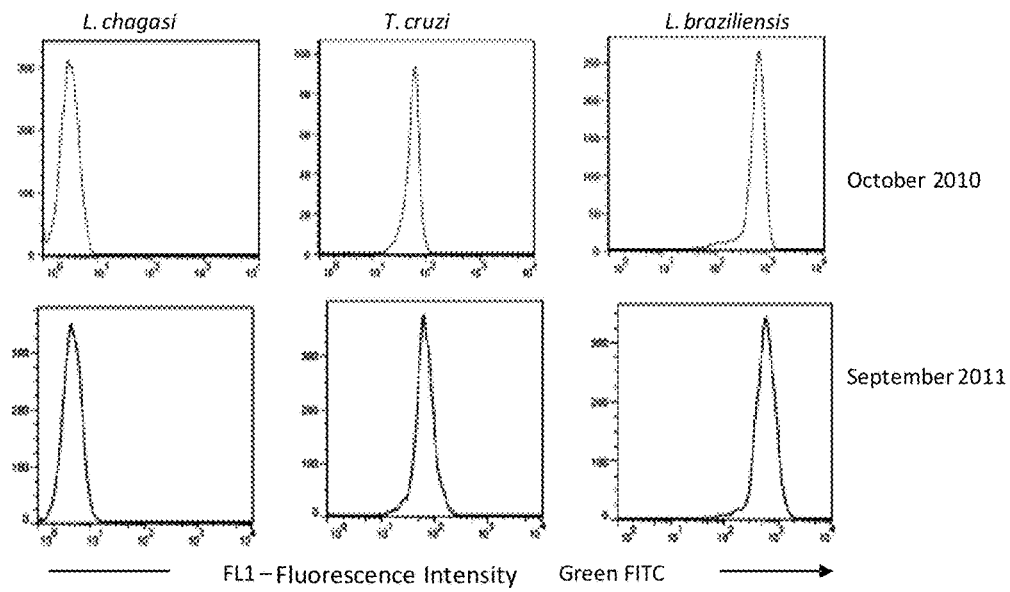
FIG. 6A and FIG. 6B show the fluorimetric stability of preparations of trypanosomatids (*T. cruzi, Leishmania chagasi, L. amazonensis* (or *L. braziliensis*)) stained with FITC system and stored for 1 year at room temperature, 4° C. and −20° C., alone (FIG. 6A) or as a mixture of parasites (FIG. 6B).
Figure 6B:
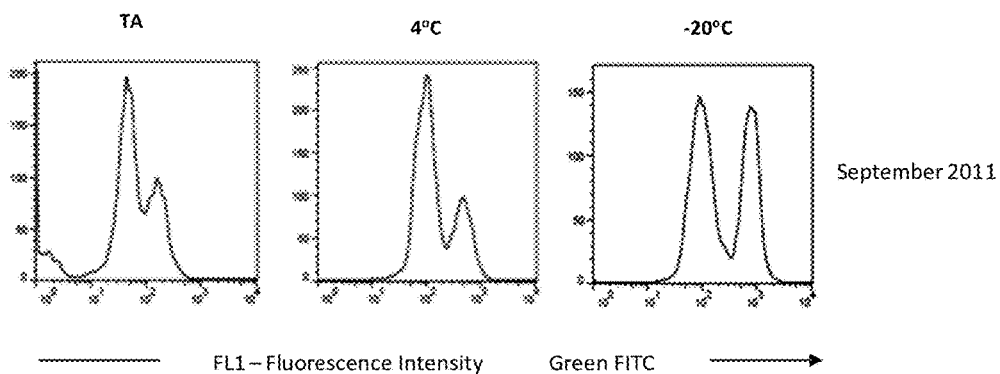
Figure 7A:
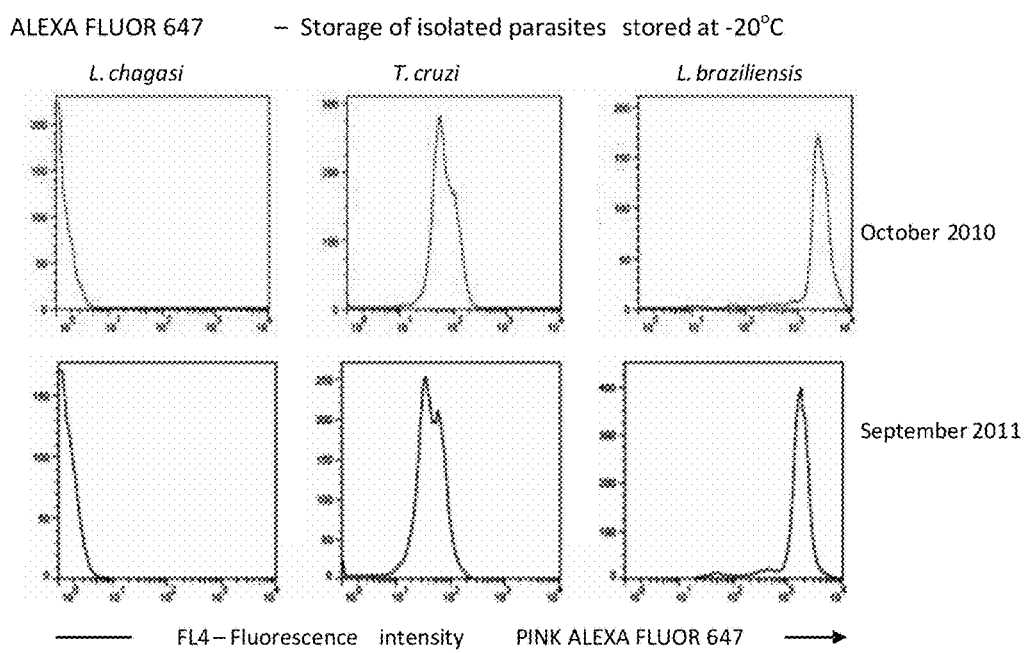
FIG. 7A and FIG. 7B show the fluorimetric stability of preparations of trypanosomatids (*T. cruzi, Leishmania chagasi, L. amazonensis* (or *L. braziliensis*)) stained with ALEXA FLUOR 647 system and stored for 1 year at room temperature, 4° C. and −20° C., alone (FIG. 7A) or as a mixture of parasites (FIG. 7B).
Figure 7B:
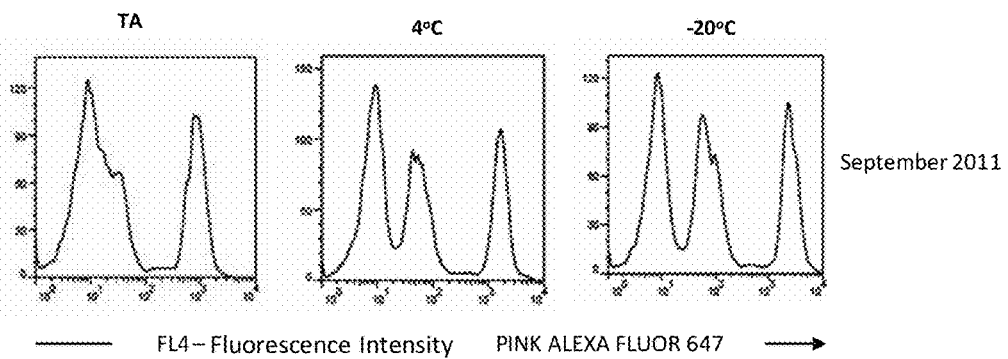

C.); the best profile was obtained with parasites stored at −20° C., as shown in FIG. 6A. The fluorimetric profile lacks stability when the parasite preparations are stored in predetermined mixing in all of the 3 storage conditions tested (room temperature, 4° C. and −20° C.), as shown in FIG. 6B. The results show that the fluorimetric profile of ALEXA FLUOR 647 staining was stable at the 3 storage conditions tested (room temperature, 4° C. and −20° C.); the best profile was obtained with parasites stored at −20° C., as shown in FIG. 7A. The fluorimetric profile has good stability when the parasite preparations are stored in predetermined mixing only in the −20° C. storage condition, and there is a substantial overlap in the storage condition at room temperature, as shown in FIG. 7B.

Thus, the analysis of results of this invention shows that the method of this invention (FC-Triplex-IgG1) is a new complementary tool applicable to the differential serological diagnosis of Chagas' disease, visceral leishmaniasis and cutaneous leishmaniasis.

The inventors observed a better stability of the parasite suspension stored separately at −20° C.

Thus, this invention reached one of its main purposes, which is the differential serological diagnosis of samples of patients with different infectious diseases.

The invention claimed is:

1. A method for differential diagnosis of diseases associated with infection of a host by trypanosomatids, said diseases including Chagas' disease and Cutaneous Leishmaniasis and Visceral Leishmaniasis, said method comprising the following steps:
   (a) differential labeling of target trypanosomatides with a first fluorescent substance to provide differentially labeled trypanosomatids, wherein a first type of trypanosomatid is labeled with the first fluorescent substance at a first concentration, a second type of trypanosomatid is labeled with the first fluorescent substance at a second concentration different from the first concentration, and a third type of trypanosomatid is labeled with the first fluorescent substance at a third concentration different from the first and second concentrations;
   (b) combining and suspending the differentially labeled trypanosomatids of step a) in a buffer solution to provide a suspension;
   (c) incubation of aliquots of the suspension with serial dilutions of a heat-inactivated human serum sample;
   (d) incubation of the aliquots from step (c) with human antibody anti-IgG1 conjugated with biotin, in a presence of streptavidin conjugated with a second fluorescent substance to provide a fluorescent labeled anti-IgG1 compound;
   (e) incubation of the aliquots from step (d) with fixative solution for cytometry to provide flow cytometry samples;
   (f) obtaining size parameters, granularity and fluorescence signal intensity measurements during analysis of the flow cytometry samples on flow cytometry equipment;
   (g) multiparametric analysis of an IgG1 reactivity profile of the flow cytometry samples, by determination of a percentage of positive fluorescent trypanosomatids relative to the fluorescence signal of the fluorescent labeled anti-IgG1 compound; and
   (h) applying a desynchronized algorithm to analytical results obtained in step (g) to determine whether the human serum sample contains antibodies indicative of Chagas' disease, Cutaneous Leishmaniasis or Visceral Leishmaniasis.

2. The method in accordance with claim 1 wherein each of the first fluorescent substance and the second fluorescent substance is a member independently selected from the group consisting of Alexa-fluor, Fluorescein Isothiocyanate, Chicago Sky Blue, Rhodamine, Phycoerythrin, and Allophycocyanine.

3. The method in accordance with claim 1 wherein the second fluorescent substance conjugated with anti-IgG1 is detected in a second fluorescence channel of the flow cytometer different from a first fluorescence channel for detecting the first fluorescent substance of the trypanosomatids.

4. The method in accordance with claim 1 wherein the algorithm of the step (h) further comprises steps to detect and analyze anti-*Leishmania chagasi*, anti-*Trypanosoma cruzi*, anti-*Leishmania amazonensis* and/or anti-*Leishmania braziliensis* present in the same human serum sample.

5. The method according to claim 1 wherein steps of the algorithm comprise detecting a percentage of positive fluorescent trypanosomatids in a series of pre-established dilutions of the human serum sample.

* * * * *